United States Patent [19]
Kabanov et al.

[11] Patent Number: 6,054,492
[45] Date of Patent: Apr. 25, 2000

[54] FLUORINATED COPOLYMERIC PHARMACEUTICAL ADJUNCTS

[75] Inventors: Alexander V. Kabanov, Omaha, Nebr.; Serguei V. Vinogradov, Moscow, U.S.S.R.

[73] Assignee: Supratek Pharma Inc., Quebec, Canada

[21] Appl. No.: 08/926,214

[22] Filed: Sep. 9, 1997

Related U.S. Application Data

[60] Provisional application No. 60/025,965, Sep. 9, 1996, and provisional application No. 60/042,740, Apr. 7, 1997.

[51] Int. Cl.$^7$ .............................. C07C 43/00; C07C 43/10
[52] U.S. Cl. ........................ 514/772; 514/785; 514/788; 514/937; 514/941; 514/975; 525/56; 525/326.9; 525/327.1; 525/329.4; 525/403; 525/408; 525/409; 525/410; 525/411; 525/417; 527/300; 527/313; 527/315; 528/401; 528/402
[58] Field of Search ........................................ 514/772, 785, 514/788, 937, 941, 975; 525/56, 326.9, 327.1, 329.4, 403, 408, 409, 410, 411, 417; 527/300, 313, 315; 528/401, 402; 536/123.1; 560/158, 179, 180, 182, 184; 564/159; 568/615; 588/188, 189, 159; 548/266.2, 266.6, 267.4, 519, 523, 524; 546/255, 256

[56] References Cited

U.S. PATENT DOCUMENTS

| | | | |
|---|---|---|---|
| 4,059,613 | 11/1977 | Nakamura et al. | 560/26 |
| 4,079,084 | 3/1978 | Houghton | 260/615 BF |
| 4,873,083 | 10/1989 | Hunter et al. | |
| 4,917,930 | 4/1990 | McCormick et al. | |
| 4,937,070 | 6/1990 | Hunter | |
| 5,035,841 | 7/1991 | Costello et al. | |
| 5,078,995 | 1/1992 | Hunter et al. | |
| 5,470,568 | 11/1995 | Lee | |
| 5,494,660 | 2/1996 | Hunter et al. | |
| 5,510,103 | 4/1996 | Yokoyama et al. | |
| 5,554,372 | 9/1996 | Hunter | |
| 5,591,715 | 1/1997 | Coon et al. | |
| 5,674,911 | 10/1997 | Emanuele et al. | |
| 5,696,090 | 12/1997 | McGregor et al. | |
| 5,696,298 | 12/1997 | Emanuele et al. | |

FOREIGN PATENT DOCUMENTS

| | | |
|---|---|---|
| WO 86/07539 | 12/1986 | WIPO |
| WO 92/00101 | 1/1992 | WIPO |
| WO 92/16484 | 10/1992 | WIPO |

*Primary Examiner*—Frederick Krass
*Attorney, Agent, or Firm*—Mathews, Collins, Shepherd & Gould, P.A.

[57] ABSTRACT

Block copolymers containing a fluorinated hydrocarbon unit, a hydrocarbon unit, and a poly(oxyethylene) unit are useful in fluid formulations of pharmaceutical agents. A typical embodiment is:

$$C_{11}H_{23}-CONHC_2H_4NHCO-C_8F_{16}-CONHC_2H_4NHCOO-(C_2H_4O)_{34}-H.$$

12 Claims, No Drawings

FLUORINATED COPOLYMERIC PHARMACEUTICAL ADJUNCTS

CROSS-REFERENCE TO RELATED APPLICATIONS

The benefit of U.S. Provisional Patent Application Ser. No. 60/025,965 filed Sep. 9, 1996 and U.S. Provisional Patent Application Ser. No. 60/042,740 filed Apr. 7, 1997, both of which are entitled "FLUORINATED COPOLYMERIC PHARMACEUTICAL ADJUNCTS", is claimed.

BACKGROUND OF THE INVENTION

The present invention pertains to block copolymer of the formula:

$$R^1-L^1-\{R^2-L^2-M\}_w-L^4-R^4-L^3-R^3 \quad \text{IA.}$$

in which:
  either (i) $R^1$ is a monovalent fluorinated hydrocarbon of 2 to 50 carbon atoms and $R^2$ is a divalent hydrocarbon of 2 to 50 carbon atoms or (ii) $R^1$ is a monovalent hydrocarbon of 2 to 50 carbon atoms and $R^2$ is a divalent fluorinated hydrocarbon of 2 to 50 carbon atoms;
  $R^3$ is (i) hydrogen, (ii) a monovalent fluorinated hydrocarbon of 2 to 50 carbon atoms, or (iii) a monovalent hydrocarbon of 2 to 50 carbon atoms;
  $R^4$ is (i) a bond if $R^3$ is hydrogen; (ii) a divalent hydrocarbon of 2 to 50 carbon atoms if $R^3$ is a fluorinated hydrocarbon, or (iii) a divalent fluorinated hydrocarbon of 2 to 50 carbon atoms if $R^3$ is a hydrocarbon;
  each of $L^1$ and $L^2$, independently of the other, is a linking group;
  $L^3$ and $L^4$ taken together with $R^4$, is a bond if $R^3$ is hydrogen or if $R^3$ is other than hydrogen each of $L^3$ and $L^4$, taken independently is a linking group;
  M is a hydrophilic homopolymer or copolymer comprising at least three monomeric units each having the same or different pendant group containing at least atom selected from the group consisting of oxygen and nitrogen; and
  w has a value of from 1 to 100.

The present invention also pertains to improved formulations for the administration of a pharmaceutical agent containing at least one block copolymer of Formula I.

These block copolymers can have profound effects on the therapeutic profile of the drug. They can, for example, produce an improvement in the therapeutic index of the drug; i.e., either or both of a decrease in side effects and an increase in therapeutic activity. While the mechanism is not know with certainty, it appears the block copolymers result in one or more of an enhancement of transport into cells and biological barriers such as histohematic barriers which separate the target cells from the perfusing blood; a decrease in sequestration of drug in organs of reticuloendothelial system; a decrease drug metabolism; and an increase drug circulation time in the body.

Moreover with antineoplastic agents, an increase in transport of the drug to solid tumors and a reverse multiple drug resistance often can be observed.

The hydrophilic homopolymer or copolymer M will contain at least three monomeric units, each of which unit will have the same or different pendant group. Each pendant group will contain at least one atom selected from the group consisting of oxygen and nitrogen. Representative hydrophilic homopolymers or copolymers include polyethylene oxides, copolymers of ethylene oxide and propylene oxide, polysaccharides, polyacrylamides, polyglycerols, polyvinylalcohols, polyvinylpyrrolidones, polyvinylpyridine N-oxides, copolymers of vinylpyridine N-oxide and vinylpyridine, polyoxazolines, and polyacroylmorpholines.

Preferably M is $$-\!\!\left[CH_2-CH_2-O\right]_{\overline{m}}\!\!-,$$

a copolymer of $$-\!\!\left[CH_2-CH_2-O\right]_{\overline{m}}\!\!- \text{ and } -\!\!\left[C_3H_6-O\right]_{\overline{j}}\!\!-,$$

$$-\!\!\left[CH_2-\underset{\underset{NH_2}{\underset{|}{C=O}}}{CH}\right]_{\overline{m}}\!\!-, \quad -\!\!\left[CH_2-\underset{OH}{\underset{|}{CH}}\right]_{\overline{m}}\!\!-,$$

[structures: pyrrolidone-substituted and imidazole-substituted vinyl units]

[structures: morpholine-substituted and pyridine N-oxide-substituted vinyl units]

in which each of m and j has a value of from 3 to 5000.

One preferred subgroup includes block copolymers of the formula:

$$R^1-L^1-R^2-L^2-(C_2H_4O)_n-L^4-R^4-L^3-R^3 \quad \text{IB.}$$

in which:
  (i) $R^1$ is a monovalent fluorinated hydrocarbon of 2 to 50 carbon atoms and $R^2$ is a divalent hydrocarbon of 2 to 50 carbon atoms or (ii) R I is a monovalent hydrocarbon of 2 to 50 carbon atoms and $R^2$ is a divalent fluorinated hydrocarbon of 2 to 50 carbon atoms;
  n has a value of from 3 to 50 or higher; i.e. 3 to about 200;
  $R^3$ is (i) hydrogen, (ii) a monovalent fluorinated hydrocarbon of 2 to 50 carbon atoms, or (iii) a monovalent hydrocarbon of 2 to 50 carbon atoms;
  $R^4$ is (i) a bond if $R^3$ is hydrogen; (ii) a divalent hydrocarbon of 2 to 50 carbon atoms if $R^3$ is a fluorinated hydrocarbon, or (iii) a divalent fluorinated hydrocarbon of 2 to 50 carbon atoms if $R^3$ is a hydrocarbon;
  each of $L^1$ and $L^2$, independently of the other, is a linking group; and
  $L^3$ and $L^4$ taken together with $R^4$, is a bond if $R^3$ is hydrogen or if $R^3$ is other than hydrogen each of $L^3$ and $L^4$, taken independently is a linking group.

Within this subgroup, particularly preferred block copolymers are those of the formula:

$$R^1-L^1-\{R^2-L^2-M\}_w-L^4-R^4-L^3-R^3 \quad \text{IC.}$$

in which:
  either $R^1$ is a monovalent hydrocarbon of 2 to 50 carbon atoms;

$R^2$ is a divalent fluorinated hydrocarbon of 2 to 50 carbon atoms;

(i) $R^3$ is hydrogen, $R^4$, $L^3$, and $L^4$ taken together are a bond or (ii) $R^3$ is a monovalent hydrocarbon of 2 to 50 carbon atoms, $R^4$ is a divalent fluorinated hydrocarbon of 2 to 50 carbon atoms, and each of $L^1$ and $L^2$, independently of the other, is a linking group;

M is a hydrophilic homopolymer or copolymer comprising at least three monomeric units each having the same or different pendant group containing at least atom selected from the group consisting of oxygen and nitrogen; and w has a value of from 1 to 100.

These block copolymers can be viewed as compose of at least three units: a fluorocarbon block, a hydrocarbon block, and a polyoxyethylene block. In a first embodiment, in which $R^3$ is hydrogen and $L^3$ and $L^4$ taken together with $R^4$ are a bond, the polyoxyethylene block constitutes one terminus of the copolymer with one of either the fluorocarbon block or the hydrocarbon block constituting the other terminus ($R^1$) and the other ($R^2$) positioned between. This first embodiment may be viewed as encompassing compounds of the formula:

$$C_xF_yH_x{-}L^1{-}C_qH_{2q}{-}L^2{-}(C_2H_4O)_n{-}H \qquad \text{IIA.}$$

in which x has a value of from 2 to 50; y has a value of from 1 to 2x+1, preferably x to 2x+1; z has a value of 2x−y+1; q has a value of from 2 to 50; n has a value of from 3 to 200; and each of $L^1$ and $L^2$, independently of the other, is a linking group, and compounds of the formula:

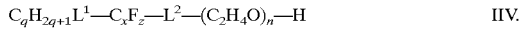
$$C_qH_{2q+1}L^1{-}C_xF_z{-}L^2{-}(C_2H_4O)_n{-}H \qquad \text{IIV.}$$

in which x, q, n, $L^1$, and $L^2$ are as just defined; y has a value of from x to 2x; and z has a value of 2x−y.

In a second embodiment, two fluorocarbon blocks or two hydrocarbon blocks constitute the termini ($R^1$ and $R^3$) while the other bracket the central the polyoxyethylene block. This second embodiment may be viewed as encompassing compounds of the formula:

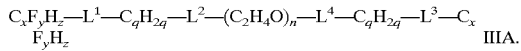
$$C_xF_yH_z{-}L^1{-}C_qH_{2q}{-}L^2{-}(C_2H_4O)_n{-}L^4{-}C_qH_{2q}{-}L^3{-}C_xF_yH_z \qquad \text{IIIA.}$$

in which x has a value of from 2 to 50; y has a value of from 1 to 2x+1, preferably from x to 2x+1; z has a value of 2x−y+1; q has a value of from 2 to 50; n has a value of from 3 to 200; and each of $L^1$, $L^2$, $L^3$, and $L^4$, independently of the other, is a linking group, and compounds of the formula:

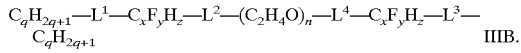
$$C_qH_{2q+1}{-}L^1{-}C_xF_yH_z{-}L^2{-}(C_2H_4O)_n{-}L^4{-}C_xF_yH_z{-}L^3{-}C_qH_{2q+1} \qquad \text{IIIB.}$$

in which x, q, n, $L^1$, $L^2$, $L^3$, and $L^4$ are as just defined; y has a value of from x to 2x; and z has a value of 2x−y.

In the fluorocarbon group $C_xF_yH_z{-}$, x has a value of from 2 to 50; i e., there can be from 2 to 50 carbon atoms. The fluorocarbon group will have at least as many fluorine atoms; i.e., there will be at least x fluorine atoms. If not perfluorinated, the remaining valence bonds of the fluorocarbon group will be satisfied with hydrogen atoms.

Differences in properties can be observed depending upon the nature of $R^1$ and $R^2$. Block copolymers of Formulas IA, IIA and IIIA in which $R^1$ is a monovalent fluorinated hydrocarbon and $R^2$ is a divalent hydrocarbon tend to be very hydrophobic and interaction with cell membranes and tissues is reduced. These copolymers produce very stable micellar forms of drugs which do not interact with non-target tissues in the body, making them useful as micellar microcontainers for delivery of the drug with decreased drug metabolism and liver uptake. In the block copolymers of Formulas IA, IIA and IIIA, q preferably has a value of 6 or more.

Block copolymers of Formulas IB, IIB and IIIB in which $R^1$ is a monovalent hydrocarbon and $R^2$ is a divalent fluorinated hydrocarbon are membranetropic, leading to their activity in MDR cells, which is a consequence of interaction of the copolymer and the cells. Mixtures of the block copolymers produce formulations which provide both the micelle-mediated drug delivery and anti-MDR activity and related activity associated with surfactant interactions with cell membranes. The block copolymers of Formula IB, IIB and IIIB are preferred.

The linking groups $L^1$, $L^2$, $L^3$, and $L^4$ generally do not contribute to the final utility of the compounds but serve to covalently join the blocks of the copolymer chain. Accordingly a wide variety of divalent linking groups can be employed.

Linking can be accomplished by a number of reactions, many of which have been described generally in conjugate chemistry. These can involve a terminal hydroxyl group on a $R^5{-}O{-}(C_2H_4O){-}H$ block, in which $R^5$ is hydrogen or a blocking group such as alkyl, and an appropriate group on the $C_xF_{y\,Hz}{-}C_qH_{2q}{-}$ block, the two being joined directly or indirectly; i.e., through a third component. Alternatively a terminal group can be converted to some other functional group, as for example amino, which then is allowed to react with either with the next block component or another linking component. The linking group thus may be formed either by reactively involving a terminal group of a block or by replacing the terminal group. For example, a carboxylic acid group can be activated as with N,N'-dicyclohexylcarbodiimide and then allowed to react with an amino or hydroxy group to form an amide or ether respectively. Anhydrides and acid chlorides will produce the same links with amines and alcohols. Alcohols can be activated by carbonyldiimidazole and then linked to amines to produce urethane linkages. Alkyl halides can be converted to an amines or allowed to react with an amine, diamines, alcohols, or diol. A terminal hydroxy group of the $R^5{-}O{-}(C_2H_4O){-}H$ block can be oxidized to form the corresponding aldehyde or ketone. This aldehyde or ketone then is allowed to react with a precursor carrying a terminal amino group to form an imine which, in turn, is reduced, as with sodium borohydrate to form the secondary amine. See Kabanov et al., *J. Controlled Release*, 22:141 (1992); *Meth. Enzymol.*, XLVII, Hirs & Timasheff, Eds., Acad. Press, 1977. The linkage thereby formed is the group -NH-, replacing the terminal hydroxyl group of the $R^5{-}O{-}(C_2H_4O){-}H$ block.

Alternatively, a terminal hydroxyl group on the $R^5{-}O{-}(C_2H_4O){-}H$ polymer can be allowed to react with bromoacetyl chloride to form a bromoacetyl ester which in turn is allowed to react with an amine precursor to form the $-NH-CH_2-C(O)-$ linkage. *Immobilized Enzymes*, Berezin et al., Eds., MGU, Moscow, 1976, ie., $-NH-CH_2-C(O)-$.

The bromoacetyl ester of a $R^1-R^2-R^3-H$ polymer, prepared as described above, also can be allowed to react with a diaminoalkane of the formula $NH_2-C_qH_{2q}-NH_2$ which in turn is allowed to react with a acid precursor of the formula $C_xF_yH_z$—COOH, or an activated derivative thereof such as an acid chloride or anhydride, to yield a compound of the formula:

$C_xF_yH_z$—CO—NH—$C_qH_{2q}$—NHCH$_2$COO—R$^1$—R$^2$—R$^3$H.   IV.

The bromoacetyl ester also can be allowed to react with a cyanide salt to form a cyano intermediate. See, e.g., Sekiguchi et al., *J. Biochem.*, 85, 75 (1979); Tuengler et al., *Biochem. Biophys. Acta*, 484, 1 (1977); Browne et al, *BBRC*, 67 126 (1975); and Hunter et al., *J.A.C.S.*, 84, 3491 (1962). This cyano intermediate then can be converted to an imido ester, for instance by treatment with a solution of methanol and hydrogen chloride, which is allowed to reacted with a amine precursor to form a —NH—C(NH$_2^+$)CH$_2$C(O)— linkage.

A terminal hydroxyl group also can be allowed to react with 1,1'-carbonyl-bis-imidazole and this intermediate in turn allowed to react with an amino precursor to form a —NH—C(O)O— linkage. See Bartling et al., *Nature*, 243:342 (1973).

A terminal hydroxyl also can be allowed to react with a cyclic anhydride such as succinic anhydride to yield a half-ester which, in turn, is allowed to react with a precursor of the formula $C_xF_yH_z$—NH$_2$ using conventional condensation techniques for forming peptide bonds such as dicyclohexylcarbodiimide, diphenylchlorophosphonate, or 2-chloro-4,6-dimethoxy-1,3,5-triazine. See e.g., Means et al., *Chemical Modification of Proteins*, Holden-Day (1971). Thus formed is the —NHC(O)—(CH$_2$)$_q$C(O)O— linkage.

A terminal hydroxyl group also can be allowed to react with 1,4-butanediol diglycidyl ether to form an intermediate having a terminal epoxide finction linked to the polymer through an ether bond. The terminal epoxide function, in turn, is allowed to react with an amino precursor. Pitha et al., *Eur. J. Biochem.*, 94:11 (1979); Elling and Kula, *Biotech. Appl. Biochem.*, 13:354 (1991); Stark and Holmberg, *Biotech. Bioeng.*, 34:942 (1989).

Halogenation of a terminal hydroxyl group permits subsequent reaction with an alkanediamine such as 1,6-hexanediamine. The resulting product then is allowed to react with carbon disulfide in the presence of potassium hydroxide, followed by the addition of proprionyl chloride to generate a isothiocyanate which in turn is allowed to react with an amino precursor to yield a —N—C(S)—N—(CH$_2$)$_6$—NH— linkage. See Means et al., *Chemical Modification of Proteins*, Holden-Day (1971).

The R$^1$-R$^2$-R$^3$-H polymer chain terminating in an amino group also can be treated with phosgene and then with a precursor of the formula $C_xF_yH_z$—NH$_2$ to form a urea linkage. See Means et al., *Chemical Modification of Proteins*, Holden-Day (1971).

The block precursor terminating in an amino group also can be treated with dimethyl ester of an alkane dicarboxylic acid and the product allowed to react with an amino precursor to produce a —N—C(NH$_2^+$)—(CH$_2$)$_4$—C(NH$_2^+$)—N— linkage. See Lowe et al., *Affinity Chromatography*, Wiley & Sons (1974).

The block precursor terminating in an amino group also can be allowed to react with an alkanoic acid or fluorinated alkanoic acid, preferably an activated derivative thereof such as an acid chloride or anhydride, to form a linking group —CONH—.

Alternatively an amino precursor can be treated with an α,ω-diisocyanoalkane to produce a —NC(O)NH(CH$_2$)$_6$NHC(O)—N— linkage. See Means, *Chemical Modification of Proteins*, Holden-Day (1971).

Some linking groups thus can simply involve a simple functional group while others may comprise a spacer unit such as a polymethylene chain between two functional groups. When the linking group comprises such a polymethylene chain, it can have as few as two methylene units but preferably contains more; e.g., six or more methylene units.

The above descriptions exemplify typical strategies for the formation of linkages between the blocks of the copolymers. These procedures parallel those which are known to form conjugates of biologically active agents and other agents. As but one example, a poly(ethylene glycol) of the formula R$^5$—O—(C$_2$H$_4$O)—H in which R$^5$ is hydrogen and a diamine of the formula H$_2$N—R$^2$—NH$_2$ can be coupled utilizing 1,1'-carbonyldimidazole. This intermediate is then allowed to react with an alkanoic acid or fluorinated alkanoic acid of the formula R$^1$COOH which has been activated with N,N'-dicyclohexylcarbodiimide. The resultant block copolymers can be separated by conventional chromatography; e.g., using silica gel column. Other strategies can be used, including the general conjugation methods described by Means et al., *Chemical Modification of Proteins*, Holden-Day (1971); Glazer et al., *Chemical Modification of Proteins*, Elsevier, N.Y. (1975); *Immunotechnology Catalog & Handbook*, Pierce Chemical Co.; and *Polyethylene Glycol Derivatives* Catalog, Shearwater Polymers, Inc. (1994).

It also will be appreciated that linkages which are not symmetrical, such as —CONH— or —NHCOO—, can be present in the reverse orientation; e.g., —NHCO— and —OCONH—, respectively.

Suitable starting materials for block copolymers in which R$^1$ is a monovalent fluorinated hydrocarbon include fluoroalkylcarboxylic acids, anhydrides and acid chlorides of fluoroalkylcarboxylic acids such as monofluoroacetic acid, trifluoroacetic acid, pentafluoropropionic acid, heptafluorobutyric acid, heptafluorobutyric anhydride, heptafluorobutyrylchloride, nonafluoropentanoic acid, tridecafluoroheptanoic acid, pentadecafluorooctanoic acid, heptadecafluorononanoic acid, nonadecafluorodecanoic acid, perfluorododecanoic acid, and perfluorotetradecanoic acid; fluoroalkanols such as 2,2,3,3,4,4,4-heptafluoro-1-butanol, 2,2,3,3,4,4,5,5,6,6,7,7, 8,8,8-pentadecafluoro-1-octanol, 2,2,3,3,4,4,5,5,6,6,7,7, 8,8,9,9,9-heptadecafluoro-1 -nonanol, 2,2,3,3,4,4,5,5,6,6,7,7,8,8,9,9,10,10,10-nonadecafluoro-1-decanol, and 2,2,3,3,4,4,5,5,6,6,7,7,8,8,9,9,10,10,11,11,11-heneicosafluoro-1-undecanol; fluoroalkyl halides such as perfluoroethyl iodide, perfluoropropyl iodide, perfluorohexyl bromide, perfluoroheptyl bromide, perfluorooctyl bromide, perfluorooctyl iodide, 1,1,1,2,2,3,3,4,4,5,5,6,6,7,7, 8,8-heptadecafluoro-10-iododecane, perfluorodecyl iodide, perfluorododecyl iodide, and 1,1,1,2,2,3,3,4,4,5,5,6,6,7,7,8, 8-heptadecafluoro-10-iododecane; fluoroalkylamines, and fluoroalkylaldehydes; and the like.

Suitable starting materials for block copolymers in which R$^1$ is a monovalent hydrocarbon include carboxylic acids, anhydrides and acid chlorides of carboxylic acids such as valeric acid, valeric anhydride, 2,4-pentadienoic acid, hexanoic acid, hexanoic anhydride, hexanoyl chloride, 2-hexenoic acid, 3-hexenoic acid, 2,6-heptadienoic acid, 6-heptenoic acid, heptanoic acid, 2-octenoic acid, octanoic acid, octanoyl chloride, nonanoic acid, nonanoyl chloride, decanoic acid, decanoic anhydride, decanoyl chloride, undecanoic acid, undecanoic anhydride, undecanoyl chloride, undecelynic acid, 10-undecenoyl chloride, lauric acid, lauric anhydride, lauroyl chloride, myristoleic acid, myristic acid, myristic anhydride, myristoyl chloride, palmitic acid, palmitic anhydride, palmitoyl chloride, palmitoleic acid, heptadecanoic acid, oleic acid, oleic anhydride, oleoyl chloride, stearic acid, stearic anhydride, stearoyl chloride, nonanedecanoic acid, arachidonic acid, heneicosanoic acid, docasanoic acid, docasanoic anhydride, tricosanoic acid, tetracosanoic acid, tetracos-15-enoic acid, hexacosanoic acid, heptacosanoic acid, octacosanoic acid, triocantanoic acid, and the like; alkanols such as heptanol, octanol, nonanol, decanol, undecanol, undecyl-9-en-1-ol, dodecanol, 1-tetradecanol, hexadecanol, hexadec-11-en-1-ol, heptadecanol, oleyl alcohol, octadecanol, nonanedecanol, hexacosanol, 1-triocantanol, and the like; aldehydes such as heptaldehyde, octyl aldehyde, decyl aldehyde, undecylic aldehyde, undecylenic aldehyde, dodecyl aldehyde, tetradecyl aldehyde, oleic anhydride and the like; and alkyl amines such as hexylamine, heptylamine, octylamine, decylamine, undecylamine, dodecylamine, pentadecyl amine, hexadecyl amine, oleylamine, stearylamine, and the like.

Suitable starting materials for block copolymers in which $R^2$ is a divalent fluorinated hydrocarbon include fluorodicarboxylic acids, and anhydrides and acid chlorides of fluorodicarboxylic acids such as tetrafluorosuccinic acid, hexafluoroglutaric acid, hexafluoroglutaric anhydride, perfluoroadipic acid, perfluorosuberic acid, perfluorosebacic acid, and the like; and fluorinated alkanediols such as 2,2,3,3,4,4,5,5-octafluoro-1,6-hexanediol and 2,2,3,3,4,4,5,5,6,6,7,7,8,8,9,9-hexadecafluoro-1,10-decanediol, and the like.

Suitable starting materials for block copolymers in which R2 is a divalent hydrocarbon include dicarboxylic acids and anhydrides and acid chlorides of dicarboxylic acids such as succinic acid, pimelic acid, pimeloyl chloride, suberic acid, sebacicic acid, sebacyl chloride, azelaic acid, azelaoyl chloride, undecanedioic acid, 1,10-decanedicarboxylic acid, dodecanedioyl chloride, 1,11-undecanedicarboxylic acid, 1,12-dodecanedicarboxylic acid, 1,12-dodecanedioyl dichloride, hexadecanedioic acid, docosanedioic acid, tetracosanedioic acid, and the like; alkanediols such as 1,10-decanediol, 1,12-dodecanediol, 1,16-hexadecanediol, and the like; and diamines such as 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, and the like; and dialdehydes and semialdhydes such as succinic dialdehyde, and succinic semialdehyde, and the like.

The hydrophilic homopolymers or copolymers encompassed by M include polyethylene oxides, copolymers of ethylene oxide and propylene oxide, polysaccharides, polyacrylamides, polygycerols, polyvinylalcohols, polyvinylpyrrolidones, polyvinylpyridine N-oxides, copolymers of vinylpyridine N-oxide and vinylpyridine, polyoxazolines, and polyacroylmorpholines. These polymers are commercially available and can be synthesized as functionally terminated derivatives for subsequent conjugation by polymerization of respective monomers as described by Veronese et al., *J. Bioact. Comp. Polym.* 5:167 (1990); Sartore et al., *J. Bioact. Compat. Polym.* 9:411 (1994); Ranucci et al., *Macromol. Chem. Phys.* 195:3469 (1994); Torchilin et al., *Biochim. Biophys. Acta.* 1195:181 (1994); Torchilin et al., *J. Pharm. Sci.* 84:1049 (1995).

By way of example, a large number of monof luctional and difinctional poly-(ethylene glycol) starting materials are available. Poly(ethylene glycol) with average molecular weights of from a few hundred to 50,000, as well as monomethoxy derivatives thereof, are commercially available; e.g., mw of 200, 1,000, 5,000, 10,000, and 25,000.

The block co-polymers of the present invention are utilized in pharmaceutical compositions intended for oral, topical (including optical and transdermal as through a topical patch), rectal, vaginal, pulmonary, or parenteral (such as intramuscular, subcutaneous, intraperitoneal or intravenous) administration. These pharmaceutical compositions can take the form of tablets, capsules, lozenges, troches, powders, gels, syrups, elixirs, aqueous solutions, suspensions, micelles, emulsions, and microemulsions.

Conventional pharmaceutical formulations are employed. In the case of tablets, for example, well-known carriers such as lactose, sodium citrate, and salts of phosphoric acid can be used. Disintegrants such as starch, and lubricating agents such as magnesium stearate, sodium lauryl sulfate and talc, as are commonly used in tablets, can be present. Capsules for oral administration can include diluents such as lactose and high molecular weight polyethylene glycols. When aqueous suspensions are required for oral use, the conjugate can be combined with emulsifying and suspending agents. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by well-known ocular delivery systems such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol.

The pharmaceuticals with which the present block copolymers can be an agent that is useful for diagnostics or imaging or an agent that acts upon a cell, organ, or organism to create a change in the functioning of the cell, organ or organism. They thus include but are not limited to pharmaceutical drugs, immunoadjuvants, vaccines, and the like. Pharmaceutical agents are represented by wide variety of agents that are used in diagnostics, therapy, immunization or otherwise are applied to combat human and animal disease such as nucleic acids, polynucleotides, antibacterial agents, antiviral agents, antifungal agents, antiparasitic agents, tumoricidal or anticancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds, local anesthetics, DNA topoisomerase inhibitors (including type I and type II), brain and tumor imaging agents, free radical scavenger drugs, anticoagulants, ionotropic drugs, and neuropeptides such as endorphins.

Thus the pharmaceutical agents include non-steroidal anti-inflammatories such as indomethacin, salicylic acid acetate, ibuprofen, sulindac, piroxicam, and naproxen, anti-glaucomic agents such as timolol or pilocarpine, neurotransmitters such as acetylcholine, anesthetics such as dibucaine, neuroleptics such as the phenothiazines (for example compazine, thorazine, promazine, chlorpromazine, acepromazine, aminopromazine, perazine, prochlorperazine, trifluoperazine, and thioproperazine), rauwolfia alkaloids (for example, reserpine and deserpine), thioxanthenes (for example chlorprothixene and tiotixene), butyrophenones (for example haloperidol, moperone, trifluoperidol, timiperone, and droperidol), diphenylbutylpiperidines (for example pimozide), and benzamides (for example sulpiride and tiapride); tranquilizers such as glycerol derivatives (for example mephenesin and methocarbamol), propanediols (for example meprobamate), diphenylmethane derivatives (for example orphenadrine, benzotrapine, and hydroxyzine), and benzodiazepines (for example chlordiazepoxide and diazepam); hypnotics (for example zolpdem and butoctamide); beta-blockers (for example propranolol, acebutonol, metoprolol, and pindolol); antidepressants such as dibenzazepines (for example, imipramine), dibenzocycloheptenes (for example, amitriptyline), and the tetracyclics (for example, mianserine); MAO inhibitors (for example phenelzine, iproniazid, and selegeline); psychostimulants such as phenylethylamine derivatives (for example amphetamines, dexamphetamines, fenproporex, phentermine, amfepramone, and pemoline) and dimethylaminoethanols (for example clofenciclan, cyprodenate, aminorex, and mazindol); GABA-mimetics (for example, progabide); alkaloids (for example codergocrine, dihydroergocristine, and vincamine); anti-Parkinsonism agents utilized in (for example L-dopamine and selegeline); agents utilized in the treatment of Alzheimer's disease, cholinergics (for example citicoline and physostigmine); vasodilators (for example pentoxifyline); and cerebro active agents (for example pyritinol and meclofenoxate).

The block copolymers also can be used advantageously with anti-neoplastic agents such as paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin, antibacterial agents such as aminoglycosides including gentamicin, antiviral compounds such as rifampicin, 3'-azido-3'-deoxythymidine (AZT), and acylovir; antifungal agents such as azoles including fluconazole, macrolides such as amphotericin B, and candicidin; antiparasitic compounds such as antimonials.

The compositions also can utilize a variety of polypeptides such as antibodies, toxins such as diphtheria toxin, peptide hormones, such as colony stimulating factor, and tumor necrosis factors, neuropeptides, growth hormone, erythropoietin, and thyroid hormone, lipoproteins such as a-lipoprotein, proteoglycans such as hyaluronic acid, glycoproteins such as gonadotropin hormone, immunomodulators or cytokines such as the interferons or interleukins, hormone receptors such as the estrogen receptor.

The block copolymers also can be used with enzyme inhibiting agents such as reverse transcriptase inhibitors, protease inhibitors, angiotensin converting enzymes, 5α-reductase, and the like. Typical of these agents are peptide and nonpeptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med Chem.* 39(17): 3278–90 1966), and didanosine. Such agents can be administered alone or in combination therapy; e.g., a combination therapy utilizing saquinavir, zalcitabine, and didanosine or saquinavir, zalcitabine, and zidovudine. See, for example, Collier et al., *Antiviral Res.,* 1996 Jam. 29(1): 99.

The block copolymers also can be used with nucleic acids such as thymine, polynucleotides such as DNA or RNA polymers or synthetic oligonucleotides, which may be derivatized by covalently modifying the 5' or the 3' end of the polynucleic acid molecule with hydrophobic substituents to facilitate entry into cells. These modified nucleic acids generally gain access to the cells interior with greater efficiency. See, for example, Kabanov et al., *FEBS Lett.,* 259:327 (1990); Boutorin et al., *FEBS Lett.,* 23:1382–1390, 1989; Shea et al, *Nucleic Acids Res.,* 18:3777–3783, 1990. Additionally, the phosphate backbone of the polynucleotides has been modified to remove the negative charge (see, for example, Agris et al., *Biochemistry,* 25:6268 (1986); Cazenave and Helene in *Antisense Nucleic Acids and Proteins: Fundamentals and Applications,* Mol and Van der Krol, Eds., p. 47 et seq., Marcel Dekker, New York, 1991) or the purine or pyrimidine bases have been modified (see, for example, *Antisense Nucleic Acids and Proteins: Fundamentals and Applications,* Mol and Van der Krol, Eds., p. 47 et seq., Marcel Dekker, New York, 1991; Milligan et al. in *Gene Therapy For Neoplastic Diseases,* Huber and Laso, Eds., p. 228 et seq., New York Academy of Sciences, New York, 1994). Such nucleic acid molecules can be among other things antisense nucleic acid molecules, phosphodiester, oligonucleotide α-anomers, ethyl phospotriester analogs, phosphorothioates, phosphorodithioates, phosphoroethyletriesters, methylphosphonates, and the like (see, for example, Crooke, Anti-Cancer Drug Design 1991, 6:609; De Mesmaeker et al.,*Acc. Chem. Res.* 1995, 28: 366). The invention is used with antigene, ribozyme and aptamer nucleic acid drugs (see, for example, Stull and Szoka, *Pharm. Res.* 1995, 12:465)

Included among the suitable pharmaceutical agents are viral genomes and viruses (including the lipid and protein coat). This accounts for the possibility of using our invention with a variety of viral vectors in gene delivery; e.g. retroviruses, adenoviruses, herpes virus, pox virus, used as complete viruses of their parts. See, for example, Hodgson, *Biotechnology,* 1995, 13: 222.

The suitable pharmaceutical agents include oxygen transporters (e.g. porphines, porphirines and their complexes with metal ions), coenzymes and vitamins (e.g. NAD/NADH, vitamins B12, chlorophylls), and the like.

The suitable pharmaceutical agents further include the agents used in diagnostics visualization methods, such as magnetic resonance imaging (e.g., gadolinium (III) diethylenetriamine pentaacetic acid), and may be a chelating group (e.g., diethylenetriamine pentaacetic acid, triethylenetriamine pentaacetic acid, ethylenediaminetetraacetic acid, 1,2-diaminocyclohexane-N,N,N',N'-tetraaceticacid, N,N'-di-(2-hydroxybenzyl)ethylene diamine), N-(2-hydroxyethyl)ethylene diamine triacetic acid and the like). Such pharmaceutical agent may further include an alpha-, beta-, or gamma-emitting radionuclide (e.g., gallium 67, indium 111, technetium 99). The suitable pharmaceutical agents also include iodine-containing radiopaque molecules. The pharmaceutical agent may also be a diagnostic agent, which may include a paramagnetic or superparamagnetic element, or combination of paramagnetic element and radionuclide. The paramagnetic elements include but are not limited to gadolinium (III), dysporsium (III), holmium (III), europium (III) iron (III) or manganese (II).

The pharmaceutical adjuncts of this invention can be also used in fibrinolitic compositions with enzymes such as streptokinase, urokinase, tissue plasminogen activator or other fibrinolitic enzyme that is effective in dissolving blood clots and reestablishing and maintaining blood flow through thrombosed coronary or other blood vessels. Also these pharmaceutical adjuncts are used in compositions for treating burns, circulatory diseases in which there is an acute impairment of circulation, in particular, microcirculation, respiratory distress syndrome, as well as compositions for reducing tissue damage during angioplasty procedures. Further, the compositions of the pharmaceutical adjuncts including but not limited to aqueous solutions of the effective concentrations of these adjuncts are used to treat myocardial damage, ischemic tissue, tissue damaged by reperfusion injury, stroke, sickle cell anemia and hypothermia. These compositions are especially useful for treating vascular obstructions caused by abnormal cells which is an often complication during malaria and leukemia and are suitable as a perfusion medium for transplantation of organs. The pharmaceutical adjuncts of this invention are also suitable for use in compositions as antiinfective compounds, as well as modulators of immune response, and improved adjuvants, antigenes and vaccines.

The adjuvants suitable for use with the pharmaceutical adjuncts of this invention include but are not limited to adjuvants of mineral, bacterial, plant, synthetic or host product origin. The suitable mineral adjuvants include aluminum compounds such as aluminum particles and aluminum hydroxide. The suitable bacterial adjuvants include but are not limited to muramyl dipeptides, lipid A, Bordetella pertussis, Freund's Complete Adjuvant, lipopolysaccharides and its various derivatives, and the like. The suitable adjuvants include without limitation small immunogens, such as synthetic peptide of malaria, polysaccharides, proteins, bacteria and viruses. The antigenes that can be used with the pharmaceutical adjuncts of the present invention are compounds which, when introduced into a mammal will result in formation of antibodies. The suitable antigens include but are not limited to natural, recombinant, or synthetic products derived from viruses, bacteria, fungi, parasites and other infectious agents, as well as autoimmune disease, hormones or tumor antigens used in prophylactic or therapeutic vaccines. These antigens include components produced by enzymatic cleavage or can be compounds produced by recombinant DNA technique. Viral antigens include but are not limited to HIV, rotavirus, influenza, foot and mouth disease, herpes simplex, Epstein Barr virus, Chicken pox, pseudorabies, rabies, hepatitis A, hepatitis B, hepatitis C, measles, distemper, Venezuelan equine encephalomyelitis, Rota virus, polyoma tumor virus, Feline leukemia virus, reovirus, respiratory synticial virus, Lassa fever virus, canine parvovirus, bovine pappiloma virus, tick borne encephalitis, rinderpest, human rhinovirus species, enterovirus species, Mengo virus, paramixovirus, avian infectious bronchitis virus. Suitable bacterial antigens include but are not limited to *Bordetella pertussis, Brucella abortis, Escherichia coli*, salmonella species, salmonella typhi, streptococci, cholera, shigella, pseudomonas, tuberculosis, leprosy and the like. Also suitable antigens include infections such as Rocky mountain spotted fever and typhus, parasites such as malaria, schstosomes and trypanosomes, and fungus such as *Cryptococcus neoformans*. The protein and peptide antigens include subunits of recombinant proteins (such as herpes simplex, Epstein Barr virus, hepatitis B, pseudorabies, flavivirus, Denge, yellow fever, Neissera gonorrhoeae, malaria, trypanosome surface antigen, alphavirus, adenovirus and the like), proteins (such as diphtheria toxoid, tetanus toxoid, meningococcal outer membrane protein, streptococcal M protein, hepatitis B, influenza hemagglutinin and the like), synthetic peptides (e.g. malaria, influenza, foot and mouth disease virus, hepatitis B, hepatitis C). Suitable polysaccharide and oligosaccharide antigens originate from *haemphilis influenza, neisseria meningitides, Pseudomonas aeruginosa, Klebsiella pneumoniae, pneumococcus*.

Preferred classes of biological agents include antineoplastic agents, antibacterial agents, antiparasitic agents, CNS agents, immunomodulators and cytokines, toxins, neuropeptides and polynucleotides. Biological agents, such as certain drugs for which target cells tend to develop resistance mechanisms are also preferred. Particularly preferred biological agents include anthracyclines such as doxorubicin, daunorubicin, or carminomycin, vinca alkaloids, mitomycin-type antibiotics, bleomycin-type antibiotics, flucanazol, amphotericin B, paclitaxel and derivatives, immuno-modulators and cytokines such as interleukins and TNFS, erythropoietin, and polynucleotides, especially oligonucleotides.

The ability of the present block copolymers to alter the biological profile and activity of pharmaceutical agents can be conveniently observed in a number of experimental models. The block copolymers for example can affect the uptake of antineoplastic agents in multidrug resistant cancer cells. The multidrug resistant KBv cell line (vinblastine resistant human epidermoid carcinoma) which expresses high levels of glycoprotein P (P-gp) efflux pump (Gervasoni, et al. *Cancer Research*, 1991, 51, 4955) can be used to evaluate the effects of the block copolymers on rhodamine 123. Rhodamine 123 is a specific probe for the effects on the P-gp efflux system, which is commonly used for evaluation of the P-gp efflux function in cancer and normal cells (Jancis, et al., *Mol. Pharmacol.* 1993, 43, 51; Lee, et al., *Mol. Pharmacol.* 1994, 46, 627). The results with rhodamine 123 are indicative of the effects on the transport of all MDR class drugs, including anthracycline antibiotics. To maintain the high expression of P-gp in the KBv cells, the cells are cultured in DMEM supplemented with 10% FBS and 1 mg/ml vinblastine. The KBv cell monolayers are grown in 24-well culture plates and used in rhodamine 123 uptake experiments after reaching confluency. Confluency of all the cell monolayers is determined by visual inspection using an inverted light microscope. The uptake of rhodamine 123 in KBv cell monolayers in presence and absence of the block copolymers is examined at 37° C. over a period of 90 minutes. The culture media is removed from the KBv monolayers and replaced with an assay buffer having the following composition: NaCl (122 mM), NaHCO$_3$ (25 mM), glucose (10 mM), KCl (3 mM), MgSO$_4$ (1.2 mM), K$_2$HPO$_4$ (0.4 mM), CaCl$_2$ (1.4 mM) and HEPES (10 mM). After a thirty-minute pre-incubation at 37° C., the assay buffer is removed from the monolayers and 3.2 $\mu$M rhodamine in the assay buffer or 3.2 $\mu$M rhodamine solubilized in 0.1% (wt.) of the block copolymer are added to the monolayers. These samples are exposed to the monolayers at 37° C. for 90 minutes and uptake then stopped by removing the medium and washing the KBv monolayers three times with 0.5 ml ice-cold PBS. The KBv monolayers are solubilized in 1.0% Triton X-100 (0.5 ml) and aliquots are removed for determining cell-associated rhodamine fluorescence and protein content. Rhodamine 123 fluorescence is determined at $\lambda_{ex}$=488 nm and $\lambda_{em}$=550 nm using Shimadzu 5000 spectrophotometer; and protein content is determined using the Pierce BCA method. The concentration of rhodamine in the KBv lyzate solution can be quantitatively determined by construction of standard curves. Data from the uptake studies are expressed as amount of cell-associated rhodamine/mg protein. Each data point represents the mean ±SEM of 4 monolayers.

For the block copolymer $C_{11}F_{23}$—CONH—$C_2H_4$—NHCOO—$(C_2H_4O)_{34}$—H, the results are as follows:

| Composition studied | Cell-associated rhodamine, nmole/mg protein |
|---|---|
| Rhodamine in assay buffer | 0.26 ± 0.01 |
| Rhodamine/block copolymer | 0.32 ± 0.02 |

For the block copolymer $C_{11}F_{23}$—CONH—$C_2H_4$—NHCOO—$(C_2H_4O)_{9\text{-}10}$—H, the results are as follows:

| Composition studied | Cell-associated rhodamine, nmole/mg protein |
|---|---|
| Rhodamine in assay buffer | 0.26 ± 0.01 |
| Rhodamine/block copolymer | 0.34 ± 0.02 |

For the copolymer $C_{11}F_{23}$—CONH—$C_2H_4$—NHCOO—$(C_2H_4O)_{34}$—CONH—$C_2H_4$NHCO—$C_{11}F_{23}$, the results are as follows:

| Composition studied | Cell-associated rhodamine, nmole/mg protein |
|---|---|
| Rhodamine in assay buffer | 0.63 ± 0.04 |
| Rhodamine/block copolymer | 0.60 ± 0.02 |

For the copolymer:
$C_{11}H_{23}$—CONH$C_2H_4$NHCO—$C_8F_{16}$—CONH$C_2H_4$NHCOO—$(C_2H_4O)_{34}$—CONH$C_2H_4$NHCO—$C_8F_{16}$—NH$C_2H_4$NHCO—$C_{11}H_{23}$
the results are as follows:

| Composition studied | Cell-associated rhodamine, nmole/mg protein |
|---|---|
| Rhodamine in assay buffer | 0.54 ± 0.04 |
| Rhodamine/block copolymer | 2.80 ± 0.14 |

P-gp also controls the permeability of human intestinal epithelial cells (Caco-2) with respect to numerous pharmaceutical agents (Thiebault et al. Proc. Natl. Acad. Sci. USA 1987, 84: 7735) and surfactants such as Cremophor EL can significantly enhance the permeability of Caco-2 cells to selected peptides (Nerurkar et al., Pharm. Res., 1996, 13: 528), presumably through inhibition of drug efflux transport systems in these cells.

The effects of the fluorinated copolymers on rhodamine 123 uptake can be observed following the procedure described above, modified however by replacing KBv cells monolayers with Caco-2 cells monolayers.

The following fluorinated block copolymers were used:
A: $C_{11}H_{23}$—CONH$C_2H_4$NHCO—$C_8F_{16}$—CONH$C_2H_4$NHCOO—$(C_2H_4O)_{34}$—H
B: $C_{11}H_{23}$—CONH$C_2H_4$NHCO—$C_8F_{16}$—CONH$C_2H_4$NHCOO—$(C_2H_4O)_{34}$—CONH$C_2H_4$NHCO—$C_8F_{16}$—NH$C_2H_4$NHCO—$C_{11}H_{23}$
C: $C_{17}H_{35}$—CONH$C_2H_4$NHCO—$C_8F_{16}$—CONH$C_2H_4$NHCOO—$(C_2H_4O)_{34}$—CONH$C_2H_4$NHCO—$C_8F_{16}$—NH$C_2H_4$NHCO—$C_{17}H_{35}$
D: $C_{12}H_{25}$NHCO$C_8F_{16}$CONH$C_2H_4$NHCOO—$(C_2H_4O)_{34}$—CONH$C_2H_4$NHCO$C_8F_{16}$CONH$C_{12}H_{25}$ The control employed 10 μg/mL cyclosporin A (CSA), an inhibitor of P-gp on the uptake of rhodamine 123. The results are as follows:

| Composition studied | Cell associated rhodamine 123, nmol/mg |
|---|---|
| Rhodamine 123 in assay buffer | 0.54 ± 0.04 |
| Rhodamine 123 in CSA | 3.02 ± 0.11 |
| Rhodamine 123 in 0.1% Copolymer A | 0.38 ± 0.03 |
| Rhodamine 123 in 0.1% Copolymer B | 2.81 ± 0.14 |
| Rhodamine 123 in 0.05% Copolymer B | 4.68 ± 0.29 |
| Rhodamine 123 in 0.025% Copolymer B | 5.31 ± 0.04 |
| Rhodamine 123 in 0.1% Copolymer C | 1.77 ± 0.14 |
| Rhodamine 123 in 0.01% Copolymer C | 2.51 ± 0.25 |
| Rhodamine 123 in 0.001% Copolymer C | 1.64 ± 0.06 |
| Rhodamine 123 in 0.125% Copolymer D | 2.33 ± 0.21 |

The block copolymers also have an effect on drug uptake across the blood brain barrier as can be demonstrated in the following model. Bovine blood brain micro-vessel endothelial cells (BBMEC) are isolated from fresh cow brains using enzymatic digestion and density centrifugation as described by Miller et al. (J. Tissue Cult. Meth., 1992, 14, 217). The BBMEC are seeded at density of 50000 cells/cm² onto collagen-coated, fibronectin-treated 24-well culture plates in media consisting of 45% minimum essential medium (MEM), 45% Ham's F-12 (F12), and 10% horse serum, supplemented with antibiotics and heparin sulfate as described in Miller et al., supra. The media is will be replaced every other day with fresh media and studies are performed on confluent BBMEC monolayers (10–12 days). The uptake studies using rhodamine 123 in assay buffer and rhodamine 123 (3.2 μM) and rhodamine 123 (3.2 μM) solubilized in 0.01% (wt.) of block copolymer are performed as described supra.

For the block copolymer $C_{11}F_{23}$—CONH—$C_2H_4$—NHCOO—$(C_2H_4O)_{34}$—H, the results are as follows:

| Composition studied | Cell-associated rhodamine, nmole/mg protein |
|---|---|
| Rhodamine in assay buffer | 1.61 ± 0.25 |
| Rhodamine/block copolymer | 2.13 ± 0.13 |

The above data demonstrate that the block copolymers enhance transport of MDR drug into cells expressing P-gp efflux system and that formulation with the block copolymers increases drug efficacy. These block copolymers also increase drug transport in cells forming the blood brain barrier, an important advantage for CNS agents. A similar increase in transport is observed with intestinal cells, which also express P-gp efflux pump, thus facilitating transport of drugs which are administered orally.

The block copolymers also sensitize cancer cells with respect to anticancer drugs. This effect of the copolymers on cytotoxicity can be seen for example with anthracycline antibiotics with respect to drug-sensitive and MDR human breast carcinoma cells. Human Breast Carcinoma MCF-7 cells (ATCC HTB 22) and the MDR MCF-7/ADR subline derived from parental cells by selection with doxorubicin (Batist, et al., J. Biol. Chem., 1986, 261, 15544) were maintained in vitro as a monolayer culture in RPMI 1640 media supplemented with 10% fetal bovine serum. The cells were cultured in the drug-free medium for minimum four passages prior to experimental use. The cells then were harvested by trypsinization, plated at 2000 to 3000 cells/well in fresh medium into 96-well microtiter plates, and cultured for 1 to 2 days to allow the reattachment. The doxorubicin with or without copolymers was subsequently added at various concentrations and the cell monolayers were incubated for 2 hours at 37° C. with 5% carbon dioxide. After incubation, the cell monolayers were washed three times with D-PBS and cultured for 4 days in RPMI 1640 supplemented with 10% FBS. The drug cytotoxicity was determined by a standard XTT assay (Scudievo, et al., Cancer Research, 1988, 48, 4827). Briefly, the sterile 1 mg/ml XTT solution in RPMI 1640 containing 5 $\mu$l of 1.54 $\mu$g/ml phenazine methasulfate solution in sterile PBS was added to the cells (50 $\mu$l/well in 200 i ll of medium) and incubated for 4 to 16 hours at 37° C. with 5% carbon dioxide. After incubation, the cell monolayers were washed three times with D-PBS. The absorbance at $\lambda$420 was determined using a microplate reader. All the experiments were carried out in triplicates. SEM values were less than 10% (P<0.05).The values of $IC_{50}$ were determined from the dose response curves.

Experiments were performed in which the $IC_{50}$ of free doxorubicin were varied several folds (which is normal for this type of study) to compare the results of these experiments the ratio of $IC_{50}$ without and with copolymer was calculated. The results for the following block copolymers are as follows:

---

A. $C_{11}F_{23}$—CONH—$C_2H_4$—NHCOO—$(C_2H_4O)_{34}$—H
B. $C_{11}F_{23}$—CONH—$C_8H_{16}$—NHCOO—$(C_2H_4O)_{34}$—H
C. $C_{11}F_{23}$—CONH—$C_8H_{16}$—NHCOO—$(C_2H_4O)_{34}$CONH—
   $C_8H_{16}$—NHCO—$C_{11}F_{23}$
D. $C_{11}H_{23}$—CONHC$_2$H$_4$NHCO—$C_8F_{16}$—CONHC$_2$H$_4$NHCOO—
   $(C_2H_4O)_{34}$—CONHC$_2$H$_4$NHCO—$C_8F_{16}$—
   NHC$_2$H$_4$NHCO—$C_{11}H_{23}$
E: $C_{12}H_{25}$NHCOC$_8$F$_{16}$CONHC$_2$H$_4$NHCOO—$(C_2H_4O)_{34}$—
   CONHC$_2$H$_4$NHCOC$_8$F$_{16}$ CONHC$_{12}H_{25}$
F: $C_{17}H_{35}$—CONHC$_2$H$_4$NHCO—$C_8F_{16}$—CONHC$_2$H$_4$NHCOO—
   $(C_2H_4O)_{34}$—CONHC$_2$H$_4$NHCO—$C_8F_{16}$—
   NHC$_2$H$_4$NHCO—$C_{17}H_{35}$
G: $C_{17}H_{35}$—CONHC$_2$H$_4$NHCOO—$(C_2H_4O)_{34}$—
   CONHC$_2$H$_4$NHCO—$C_{17}H_{35}$
H: $C_{11}H_{23}$—CONHC$_2$H$_4$NHCOO—$(C_2H_4O)_{34}$—
   CONHC$_2$H$_4$NHCO—$C_{11}H_{23}$

---

The following examples will serve to further typify the nature of the invention but should not be construed as a limitation on the scope thereof.

EXAMPLE 1

A. A mixture of 3.7 g (6 mmoles) perfluorododecanoic acid (Aldrich) in 30 ml of dry dichloromethane is treated with 0.63 g (3 mmol) of N,N'-dicyclohexylcarbodiimide for 3 hours at room temperature. The solid which forms is separated by filtration and washed two times with dichloromethane. The combined filtrate and washings are evaporated in vacuum and 3.6 g of the resulting solid is dissolved in 15 ml of an absolute pyridine. This solution is used in Part C of this Example without further purification.

B. A solution of 0.18 g (1 mmol) of 1,1'-carbonyldimidazole in 10 ml of dioxane is added in small portions to 1.5 g (1 mmol) of poly(ethylene glycol), mw 1,500, (Aldrich) with constant stirring. After 1 hour at room temperature, the reaction mixture is treated with a 5-fold excess (5 mmol) of ethylenediamine and stirring is continued for additional two hours at room temperature. The product is precipitated in ether, dissolved in 5 ml of dioxane, precipitated again in ether, collected, and dried in vacuum.

C. Ten milliliters of the pyridine solution obtained in Part A and 1.4 mg of the intermediate obtained at Part B are allowed to react at room temperature for fifteen hours. The reaction mixture is then treated with 0.5 ml of methanol and the solvent removed by co-evaporation with toluene. The residue is dissolved in 10 ml of dichloromethane and placed on a 60–100 mesh silica gel column (Fisher Scientific) using a stepwise gradient of 5%, 10% and 20% methanol in dichloromethane. Eluting with 10% methanol, there is obtained in a 25% yield:

$C_{11}F_{23}$—CONH—$C_2H_4$—NHCOO—$(C_2H_4O)_{34}$—CONH—
$C_2H_4$NHCO—$C_{11}F_{23}$

Eluting with 20% methanol there is obtained in a 50% yield:

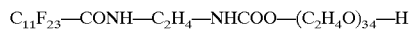

$C_{11}F_{23}$—CONH—$C_2H_4$—NHCOO—$(C_2H_4O)_{34}$—H

Both compounds are free of initial reagents, intermediates and other derivatives, as determined using thin-layer chromatography silica gel 60 F 254 plates (Riedel-de Haen,

---

| Composition studied | MCF-7 cells | | MCF-7 ADR | |
|---|---|---|---|---|
| | $IC_{50}$, ng/ml | $IC_{50}$ ratio | $IC_{50}$, ng/ml | $IC_{50}$ ratio |
| Doxorubicin in assay buffer | 1000 | — | 20000 | — |
| Doxorubicin in 0.1% Copolymer A | 560 | 1.78 | 7200 | 2.78 |
| Doxorubicin in 0.1% Copolymer B | 220 | 4.54 | 5800 | 3.44 |
| Doxorubicin in 0.1% Copolymer C | 86 | 11.6 | 5000 | 4.00 |
| Doxorubicin in assay buffer | 1000 | — | 53000 | — |
| Doxorubicin in 0.02% Copolymer D | 950 | 1.05 | 22000 | 2.41 |
| Doxorubicin in assay buffer | 850 | — | 100000 | — |
| Doxorubicin in 0.0025% Copolymer E | 800 | 1.06 | 90000 | 1.11 |
| Doxorubicin in 0.005% Copolymer E | 850 | 1 | 72000 | 1.40 |
| Doxorubicin in 0.025% Copolymer E | 750 | 1.13 | 21000 | 4.76 |
| Doxorubicin in 0.05% Copolymer E | 820 | 1.04 | 4000 | 25 |
| Doxorubicin in assay buffer | 1000 | — | 18000 | — |
| Doxorubicin in 0.05% Copolymer F | T | — | T | — |
| Doxorubicin in 0.05% Copolymer G | T | — | 2500 | 4.72 |
| Doxorubicin in 0.05% Copolymer H | T | — | T | — |

T = formulation toxic at the concentrations used.

17

Germany); eluting with 85:15 dichloromethane:methanol and developed in iodine vapor and 2% ninhydrin solution in ethanol.

EXAMPLE 2

Following the procedure of Example 1 but substituting 4.0 g of poly(ethylene glycol) mw 400, for poly(ethylene glycol) mw 1,500 in Part B, there is obtained in a 30% yield:

and in a 42% yield:

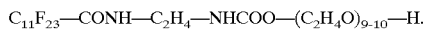

Both products elute from the silica gel column at somewhat higher methanol concentrations as compared with the products of Example 1.

EXAMPLE 3

Following the procedure of Example 1 but substituting 2.0 g of poly(ethylene glycol) mw 200, for poly(ethylene glycol) mw 1,500 in Part B, there is obtained in a 33% yield:

and in a 52% yield:

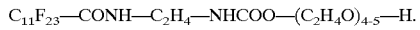

Again both products elute from the silica gel column at higher methanol concentrations as compared with the products of Example 1.

EXAMPLE 4

Following the procedure of Example 1 but substituting 5 mmol of 1,8-diamino-octane for ethylenediamine in Part B, there is obtained in a 28% yield:

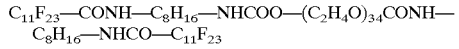

and in a 48% yield:

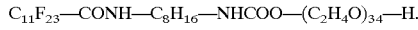

EXAMPLE 5

A. A mixture of 1.0 g of lauric acid in 25 ml of dry dichloromethane is treated with 0.5 g of N,N'-dicyclohexylcarbodiimide for 3 hours at room temperature. The solid which forms is separated by filtration and washed two times with dichloromethane. The combined filtrate and washings are evaporated in vacuum and 0.95 g of the resulting lauric anhydride is dissolved in 20 ml of an absolute pyridine. This solution is used in Part D of this Example without further purification.

B. Poly(ethylene glycol), mw 1,500, and ethylenediamine were allowed to react in the presence of 1,1'-carbonyldimidazole as described in Example 1, Part B.

C. A mixture of 2.5 g (5 mmol) of perfluorosebacic acid (Aldrich), 1.35 g (10 mmol) of 1-hydroxybenzotriazol, and 2.04 g of N,N'-dicyclohexylcarbodiimide in 30 ml of anhydrous pyridine is allowed to react for 18 hours at room temperature. The solid is removed by filtration and 10 ml of the filtrate was allowed to reacted with the intermediate of Part B of this Example for 18 hours at room temperature. A 5-fold excess (5 mmol) of ethylenediamine then was added and the resulting intermediate was purified using 60–100 mesh silica gel column using stepwise gradient of 5%, 10% and 20% methanol in dichloromethane. The yield of the intermediate was 68%.

D. Ten milliliters of the pyridine solution obtained in Part A and 1.4 mg of the intermediate obtained at Part C are allowed to react at room temperature for fifteen hours. The reaction mixture is then treated with 0.5 ml of methanol and the solvent removed by co-evaporation with toluene. The residue is dissolved in 10 ml of dichloromethane and placed on a 60–100 mesh silica gel column (Fisher Scientific) using a stepwise gradient of 5%, 10% and 20% methanol in dichloromethane. Eluting with 10% methanol, there is obtained in a 10% yield:

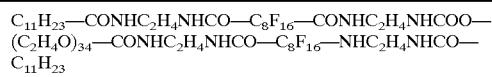

Eluting with 15% methanol, there is obtained in a 70% yield:

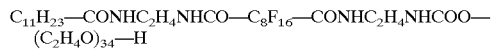

Both compounds are free of initial reagents, intermediates and other derivatives, as determined using thin-layer chromatography silica gel 60 F 254 plates (Riedel-de Haen, Germany); eluting with 85:15 dichloromethane:methanol and developed in iodine vapor and 2% ninhydrin solution in ethanol.

EXAMPLE 6

A. Diamino-modified derivative of poly(ethylene glycol), mw. 1,500, (Aldrich) was synthesized using 1,1-carbonyldiimidazole-mediated activation of the terminal hydroxyl groups, a modified method described by Hearn, *Meth. Enzymol.*, 135:102 (1987). Two grams of poly (ethylene glycol), was dissolved in 10 mL of pyridine and the solution was diluted with 40 mL of tetrahydrofuran. 1,1-Carbonyldiimidazole then was added to this solution in a 5-fold molar excess with respect to the terminal hydroxyl-groups of the poly(ethylene glycol). The reaction mixture was stirred 2 hours at a room temperature, evaporated, and carefully washed with ether. The polymer was re-dissolved in 20 mL of pyridine, poured into solution of 2 mL ethylenediamine in 40 mL of tetrahydrofuran, and stirred overnight. After evaporation the product was washed with ether, dried, re-dissolved in 40 mL of 10% methanol and passed through a Sephadex G-25 column equilibrated with the same buffer (column size: 2.5×90 cm, flow rate 4 mL/min, 8 mL fractions). Fractions were detected by colored reaction of small aliquots with ninhydrin. Fractions corresponding to diamino-modified poly(ethylene glycol) were pooled, the solvent evaporated, and the residue freeze dried. Typical yields were 1.6 to 1.8 g of diamino-modified poly(ethylene glycol).

B. A total of 4.5 g (22 mmoles) of solid N,N'-dicyclohexylcarbodiimide was added in small portions over a 5 minute period to a solution of 4.9 g. (20 mmoles) of perfluorosebacic acid (Aldrich) and 2.8 g. (20 mmoles) of p-nitrophenol (Sigma) in 60 mL of anhydrous tetrahydrofuran. The reaction mixture was stirred overnight and the dicyclohexyurea then separated by filtration. The filtrate was evaporated, re-dissolved in 40 mL of methylene chloride and subjected to absorption chromatography on silica-gel Si-60 (Merck) in methylene chloride. The yield of the di-p-nitrophenyl ester of perfluorosebacic acid was 1.4 g. (28%). Mononitrophenyl ester of perfluorosebacic acid eluted with 10% methanol and was a major byproduct (1.7 g., 32%). No unreacted perfluorosebacic acid was recovered, although about 1 g. of unreacted p-nitrophenol was isolated from the reaction mixture. The product was analyzed by thin layer chromatography (dichloromethane: methanol, 9:1): Rf=0.85 for di-p-nitrophenyl ester of perfluorosebacic acid, Rf=0.1–0.4 for mononitrophenyl ester of perfluorosebacic acid. (p-nitrophenol has Rf=0.5).

C. A total of 1.4 g. (2 mmole) of di-p-nitrophenyl ester of perfluorosebacic acid (obtained for example as in Part B) was allowed to react overnight at room temperature with 0.4 g (2.1 mmoles) of dodecylamine (Aldrich) in 30 mL of methylene-chloride. The reaction was monitored by the thin layer chromatography (dichloromethane: methanol, 9:1): Rf=0.8 for the product, the product was developed in UV and iodine vapors. In contrast to the starting diester, the product of the reaction gives brown-colored development with iodine vapors). The reaction mixture was purified by chromatography on Silica gel Si-60 using methylene chloride as an eluent. The yield of the perfluorosebacyl-mono-dodecylamide p-nitrophenyl ester was 1.2 g. (88%).

D. A total of 0.6 g. of diamino-modified poly(ethylene glycol) obtained in Part A was dissolved in 10 mL of anhydrous pyridine and then allowed to react with a 3-fold molar excess perfluorosebacyl-mono-dodecylamide p-nitrophenyl ester obtained in Part C. The reaction mixture was incubated 48 h. at a room temperature, evaporated, re-dissolved in 20 mL of methanol, and separated using the Toyopearl HW40 column equilibrated with methanol. Separation was carried out at a flow rate of 2 mL/minutes with 8 mL fractions being collected. Each fraction was analyzed by thin layer chromatography, eluting with 9:1 dichloromethane:methanol and developing with iodine vapors. Thus was obtained in a 25% yield:

This product has the same Rf as the initial diamino-modified poly(ethylene glycol) but is inert with respect to the ninhydrin.

EXAMPLE 7

Following the procedure of Example 6 but substituting 2 g of poly(ethylene glycol), mw 1500, for poly(ethylene glycol), mw. 4600 in Part A, there is obtained in 50% yield:

$C_{12}H_{25}NHCOC_8F_{16}CONHC_2H_4NHCOO-(C_2H_4O)_{104}-$
$CONHC_2H_4NHCOC_8F_{16}CONHC_{12}H_{25}$

EXAMPLE 8

Following the procedure of Example 6 but substituting 2 g of poly(ethylene glycol), mw 1500, for poly(ethylene glycol), mw. 8000 in Part A, there is obtained in 40% yield:

EXAMPLE 9

A. 4.5 g (3 mmol) of poly(ethylene glycol), mw 1500 (Aldrich) were dried by co-evaporation with anhydrous pyridine in vacuo and dissolved in 50 mL of anhydrous acetonitrile. Then 0.51 g (1.5 mmol) of 4,4'-dimethoxytrityl chloride in 30 mL of anhydrous pyridine was added to this solution dropwise under continuous stirring over a 30 minute period. The mixture was allowed to stand for additional 2 hours at room temperature and the solvents then were evaporated in vacuo. The residue was dissolved in 50 mL of dichloromethane, extracted with 5% sodium bicarbonate (2×30 mL), and applied to a Silica gel column (3×45 cm, 40–60 μm). Stepwise elution with dichloromethane-methanol solutions separated a slightly yellow mono-4,4'-dimethoxytrityl-derivative of poly(ethylene glycol) (Rf=0.6 in 9:1 dichloromethane:methanol) with an yield about 75–85%. A side product of the reaction (10–15% yield) was the 4,4'-bis-dimethoxytrityl-derivative of poly(ethylene glycol) (Rf 0.7–0.75 in the same solvent system).

B. Following the procedure of Example 6, Part A, but substituting 2 g of poly(ethylene glycol), mw 1500, and 2 mL of ethylenediamine for 4.6 g. of mono- 4,4'-dimethoxytrityl poly(ethylene glycol), 4600, obtained in Part A of this Example, and 10 g. of 1,10-diaminodecane (Aldrich) there is obtained 4.5 g. of:

$H_2NC_{12}H_{24}NHCOO-(C_2H_4O)_{104}-DMT$

C. Perfluorododecanoic acid, 0.61 g. (1 mmole), was activated with 1.5 mmoles of N,N'-dicyclohehylcarbodiimide in 20 mL of dioxane-acetonitrile, 1:1 v/v. After 10 minutes of preactivation the precipitate of dicyclohexylurea was filtered off and filtrate was added to a solution of 2 g. of $H_2NC_{12}H_{24}NHCOO-(C_2H_4O)_{104}-$ DMT in 20 mL of dioxane. The reaction mixture was stirred for 1 hour at a room temperature, evaporated, redissolved in 20 mL MeOH and separated on a Toyopearl HW-40 column (2.5×30 cm) using methanol as eluent at a flow rate of 2 ml L/min. $C_{11}F_{23}CONHC_{12}H_{24}NHCOO-(C_2H_4O)_{104}-DMT$ was eluted in 50–70 mL and low molecular mass impurities were eluted at 70–120 mL. $C_{11}F_{23}CONHC_{12}H_{24}NHCOO-(C_2H_4O)_{104}-DMT$ had an Rf of 0.1–0.4 in 9:1dichloromethane:methanol, was positive for UV and iodine vapors, and was not stained by the ninhydrin. The yield of $C_{11}F_{23}CONHC_{12}H_{24}NHCOO-(C_2H_4)_{104}-DMT$ was 1.2 g.

D. 1.2 g. of $C_{11}F_{23}CONHC_2H_{24}NHCOO-(C_2H_4O)_{104}-DMT$ were deprotected with 5% trifluoroacetic acid (TFA) in dichloromethane for 5 minutes. After evaporating the solvent the traces of TFA were carefully removed by washing with ether and gel-permeation chromatography on Toyopearl HW-40 at the conditions described in Part C to yield 0.6 g of product:

$C_{11}F_{23}CONHC_{12}H_{24}NHCOO-(C_2H_4O)_{104}-H$

This material had an Rf=0.1–0.4 in 9:1 dichloromethane:methanol, was not stained with ninhydrin or TFA, did not absorb in UV, and was stained with iodine vapor.

EXAMPLE 10

A solution of 1 g. (2 mmoles) of perfluorosebacic acid and 0.4 g. (2 mmoles) of dodecylamine in 40 mL of acetonitrile was reacted with 0.42 g. (2.2 mmoles) of N,N'-dicyclohexylcarbodiimide. Immediate formation of the dicyclohexylurea precipitate was observed. After 40 minutes, the reaction was complete as determined by disappearance of perfluorosebacic acid using thin layer chromatography (9:1 dichloromethane:methanol). The Rf was 0.8 and the product developed in both UV and iodine vapors. The residue was redissolved in 10 mL of dioxane and this solution was filtered, the solid washed with 5 mL of acetonitrile, and the filtrates combined. The filtrate was mixed with 20 mL of the dioxane solution of 1.5 g diamino-modified poly(ethylene oxide), mw. 1500, obtained in Example 6, Part A. This solution allowed to react overnight with 0.42 g (2.2 mmoles) of N,N'-dicyclohexylcarbodiimide at a room temperature. The solvents then were evaporated and the residue was carefully washed with ether, dried, redissolved in methanol, and purified on the Toyopearl HW-40 column equilibrated with methanol (column size: 2.5×30 cm, flow rate 2 mL/min, 8 mL fractions). Eluting at 40–70 mL there is obtained in a 40% yield:

$C_{12}H_{25}NHCOC_8F_{16}CONHC_2H_4NHCOO-(C_2H_4O)_{34}-CONHC_2H_4NHCOC_8F_{16}CONHC_{12}H_{25}$

EXAMPLE 11

Following the procedure of Example 5, but substituting 1 g of lauric acid for 2 g of stearic acid in Part A, there is obtained in 15% yield:

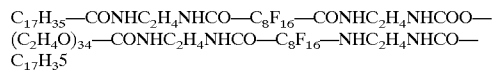

$C_{17}H_{35}-CONHC_2H_4NHCO-C_8F_{16}-CONHC_2H_4NHCOO-(C_2H_4O)_{34}-CONHC_2H_4NHCO-C_8F_{16}-NHC_2H_4NHCO-C_{17}H_{35}$

EXAMPLE 12

A composition suitable for parental administration is prepared with the following copolymers:

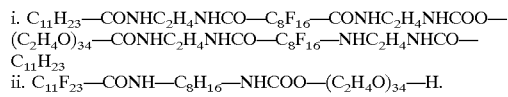

i. $C_{11}H_{23}-CONHC_2H_4NHCO-C_8F_{16}-CONHC_2H_4NHCOO-(C_2H_4O)_{34}-CONHC_2H_4NHCO-C_8F_{16}-NHC_2H_4NHCO-C_{11}H_{23}$ ii. $C_{11}F_{23}-CONH-C_8H_{16}-NHCOO-(C_2H_4O)_{34}-H.$

Twenty-five milligrams of copolymer i and 500 mg of copolymer ii are dissolved in 50 mL of RPMI 1640 at 4° C. The mixture is incubated for 30 minutes at 37° C. and then sterilely filtered through a 0.22 μm filter. This is mixed with a solution of 10 mg of sterile lyophilized daunorubicin powder dissolved in 50 mL of RPMI and incubated for 30 minutes at 37° C.

The composition can be stored in the dark at room temperature for 7 days without any essential loss of activity or can be lyophilized and stored for at least 1 year in the dark at room temperature.

EXAMPLE 13

A composition suitable for parental administration is prepared with the following copolymers:

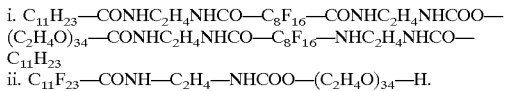

i. $C_{11}H_{23}-CONHC_2H_4NHCO-C_8F_{16}-CONHC_2H_4NHCOO-(C_2H_4O)_{34}-CONHC_2H_4NHCO-C_8F_{16}-NHC_2H_4NHCO-C_{11}H_{23}$ ii. $C_{11}F_{23}-CONH-C_2H_4-NHCOO-(C_2H_4O)_{34}-H.$

One hundred milligrams of copolymer i and 500 mg of copolymer ii are dissolved in 50 mL of PBS at 4° C. The mixture is incubated for 30 minutes at 37° C. and then sterilely filtered through a 0.22 gm filter. This is mixed with a solution of 1 mg of sterile lyophilized daunorubicin powder and 5 mg of glucose dissolved in 50 mL of PBS and the mixture is incubated for 30 minutes at 37° C.

The composition can be stored in the dark at room temperature for 7 days without any essential loss of activity or can be lyophilized and stored for at least 1 year in the dark at room temperature.

EXAMPLE 14 A composition suitable for parental administration is prepared with the following copolymer:

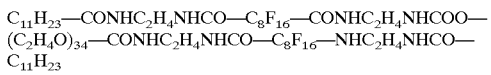

$C_{11}H_{23}-CONHC_2H_4NHCO-C_8F_{16}-CONHC_2H_4NHCOO-(C_2H_4O)_{34}-CONHC_2H_4NHCO-C_8F_{16}-NHC_2H_4NHCO-C_{11}H_{23}$

One hundred milligrams of sodium ascorbate are dissolved in a 9% aqueous solution of sodium chloride. To one-half of this solution are added at 4° C. 100 mg of the indicated copolymer. The mixture is incubated for 30 minutes at 37° C and then sterilely filtered through a 0.22 gm filter. Separately 10 mg of sterile lyophilized daunorubicin powder and 50 mg of glucose are dissolved in the remaining sodium ascorbate-sodium chloride solution and the two solutions are mixed and incubated for 30 minutes at 37° C.

This composition can be stored for 30 days in the dark at room temperature without any essential loss of activity or can be lyophilized and stored for at least 1 year in the dark at room temperature.

EXAMPLE 15

Critical micelle concentration (CMC) is a concentration below which surfactant molecules are deaggregated and present in solution in a form of single molecules (unimers) and above which at least part of surfactant molecules are aggregated into micelles. Many methods determine CMC by measuring a dependence of some physico-chemical parameter of the solution of the surfactant on the surfactant concentration, e.g., surface tension, conductivity, pressure of solvent vapor. These dependencies usually reveal a break or leveling-off at CMC. Other methods use hydrophobic probes that change their physico-chemical properties (e.g., fluorescence, UV light absorbency, solubility) after solubilization into the micelles. See e.g., Martin et al. *Physical Pharmacy*, Lea & Febiger, (1993).

The CMC in the solution of the block copolymer were determined by two independent methods: (1) the surface tension technique described in Kabanov et al,. *Macromolecules,* 28: 2303 (1995) and (2) measurement of fluorescence of rhodamine b 123.

(1) Surface tension technique: Surface tension in sample solutions (0.000001 to 20 wt %) was determined by the ring-tearing technique at 37° C. using torsion weight with a thermostatic cell unit (the error in the temperature determination was ±0.1° C.). CMC was determined as the break point in the surface tension vs. concentration curve after which the surface tension was leveled off.

(2) Fluorescence of rhodamine 123: Two milliliter samples of the solution (0.00001 to 5 wt %) were mixed with 1 nmol of dry rhodamine 123 and agitated for min at 37° C. to achieve complete dissolution of the dye and temperature equilibration. The sample solutions were placed in the Shimadzu 5000 spectrofluorimeter with a thermostatic cell unit at 37° C. and the intensity of fluorescence emission was measured at 540 nm after exciting at 508 nm. CMC was determined as a break point at the dependence of the fluorescence on the concentration of the surfactant.

The CMC was determined for the following fluorinated copolymers:

A: $C_{11}F_{23}CONHC_2H_4NHCOO-(C_2H_4O)_{34}-H$
B: $C_{11}H_{23}CONHC_8F_{16}NHCOO-(C_2H_4O)_{34}-H$
C: $C_{11}F_{23}CONHC_8H_6NHCOO-(C_2H_4O)_{34}-H$
D: $C_{11}F_{23}CONHC_{12}H_{24}NHCOO-(C_2H_4O)_{104}-H$

The results are as follows:

| Compound | CMC, % wt | |
|---|---|---|
| | Surface tension | Rhodamine 123 |
| Copolymer A | 1.0 | 0.4 |
| Copolymer B | 0.2 | 0.2 |
| Copolymer C | 0.006 | 0.006 |
| Copolymer D | 0.2 | 0.125 |

EXAMPLE 16

A. 4 g (7 mmoles) of perfluorodecanoic acid (Aldrich) dissolved in 30 ml of dry dichloromethane is treated with 1.5 g (7 mmoles) of N,N'-dicyclohexylcarbodiimide for 3 hours at room temperature. The solid, which forms is separated by filtration and washed two times with dichloromethane. The combined filtrate and washings are evaporated in vacuum and dissolved in 15 ml of absolute pyridine, mixed with 5 ml of the solution of 0.36 g (7 mmol) of ethylenediamine in absolute pyridine and allowed to react at room temperature for 15 hours. After that the reaction mixture is treated with 0.5 ml of methanol and the solvent removed by co-evaporation with toluene. The residue is dissolved in 10 ml of dichloromethane and placed on a 60–100 mesh silica gel column (Fisher Scientific) using a gradient of methanol in dichloromethane. The product of the reaction, $C_{11}F_{23}CONHCH_2CH_2NH_2$, is collected, dried in vacuo and then redissolved in 10 ml of dimethyl sulfoxide.

B. The solution of $C_{11}F_{23}CONHCH_2CH_2NH_2$ obtained in Part A is added in small portions to the solution of 50 g (10 mmol) of dextran, mw 10,000 (Sigma) in 100 ml of dimethyl sulfoxide. The reaction mixture was incubated during 48 hours at 40° C. in the presence of 0.62 g (10 mmol) of sodium cyanoborohydride (Sigma). The copolymer was dialyzed against water for 5 days using Spectra/Por membranes and then purified by high-pressure liquid chromatography using Silasorb C18 column in the gradient of acetonitrile. There is obtained 35 g of:

EXAMPLE 17

Following the procedure of Example 16 but substituting 1.2 g of 1,8-diamino-octane for 0.36 g (7 mmol) of ethylenediamine in Part A there is obtained 40 g of:

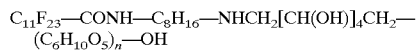

EXAMPLE 18

A. The carboxyterminated polyvinylpyrrolidone was obtained using method described by Torchilin et al. (*J. Pharm. Sci.* 84:1049, 1995). Polyvinylpyrrolidone was synthesized by chain transfer free radical polymerization of 50% wt. N-vinyl-pyrrolidone (Sigma) in isopropoxyethanol with 1% wt. 2,2'-azoisobutyronitrile (Sigma) as initiator. The mw of the polymer obtained was about 6,000 as determined by viscosinietry and gel-permeation chromatography on Sephadex G25. The terminal OH group of polyvinylpyrrolidone was converted into COOH group by activating the OH group with 4-nitrophenyl chlorophormate and subsequently coupling it with glycine as described by Sartore et al., *J. Bioact. Compat. Polym.* 9:411 (1994).

B. Six grams (1 mmole) of carboxyterminated polyvinylpyrrolidone obtained in Part A dissolved in 30 ml of dry dioxane is treated with 0.2 g of N,N'-dicyclohexyl-carbodiimide for 3 hours at room temperature and then reacted with 6 g of $C_{11}F_{23}-CONHCH_2CH_2NH_2$ obtained in Example 16, Part A for 15 hours at room temperature. The reaction mixture was then dialyzed against water for 5 days using Spectra/Por membranes and then purified by high-pressure liquid chromatography using Silasorb C18 column in the gradient of acetonitrile. There is obtained 4 g of:

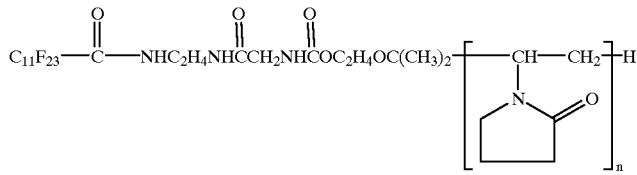

EXAMPLE 19

A. The carboxyterminated polyaryloylmorpholine was obtained using method described by Torchilin et al. (*J. Pharm. Sci.,* 84:1049, 1995). The monomer was synthesized by acylation of morpholine (Aldrich) with acryloyl chloride (Aldrich), which was then polymerized in water with 1% wt. 2,2'-azoisobutyronitrile (Sigma) as initiator and 2-mercaptoacetic acid as chain transfer reagent (Ranucci et al. *Macromol. Chem. Phys.* 195:3469, 1994). The mw of the polymer obtained was ca. 8,000 as determined by viscosimetry and gel-permeation chromatography on Sephadex G25.

B. Following the procedure of Example 18 but substituting 8 g of carboxyterminated polyaryloylmorpholine for 6 g of carboxyterminated polyvinylpyrrolidone in Part B there is obtained 4.5 g of:

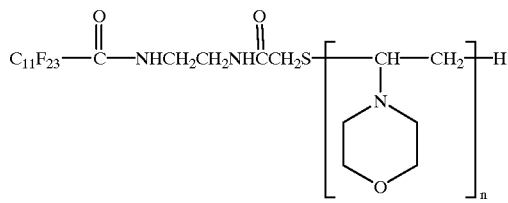

EXAMPLE 20

A. The carboxyterminated polyacrylamide was obtained using method described by Torchilin et al. (*Biochim. Biophys. Acta.* 1195:181, 1994). Ten percent by weight of acrylamide (Aldrich) was polymerized in dioxane with 1% wt. 2,2'-azoisobutyronitrile (Sigma) as initiator and 2-mercaptoacetic acid as chain transfer reagent. The mw of the polymer obtained was ca. 5,000 as determined by viscosimetry and gel-permeation chromatography on Sephadex G25.

B. Following the procedure of Example 18 but substituting 5 g of carboxyterminated polyacrylamide for 6 g of carboxyterminated polyvinylpyrrolidone in Part B, there is obtained 2.7 g of:

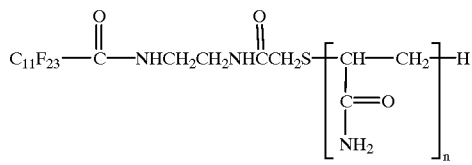

EXAMPLE 21

A. Following the procedure of Example 16, Part A, but substituting 1.2 g of 1,12-diaminododecane (Aldrich) for 0.36 g of ethylenediamine, there is obtained 1.1 g of:

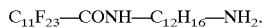

B. Following the procedure of Example 20 but substituting the same molar excess of $C_{11}F_{23}$—CONH—$C_{12}H_{16}$—$NH_2$ for $C_{11}F_{23}$—CONHCH$_2$CH$_2$NH$_2$ in Part B, there is obtained 1.2 g of:

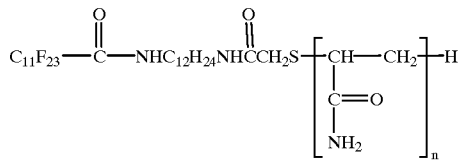

EXAMPLE 22

Following the procedure of example 20 but substituting vinyltriazole monomer for acrylamide monomer in part a there is obtained 2.2 g of:

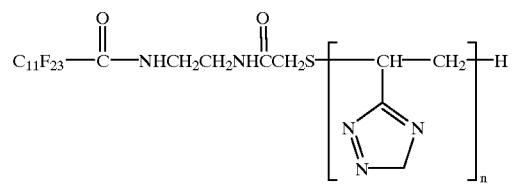

What is claimed is:

1. A compound having the formula:

$$C_qH_{2q+1}-L^1-\{R^2-L^2-M\}_w-L^4-R^4-L^3-R^3$$

in which:

q has a value of from 2 to 50;

w has a value of from 1 to 100;

$L^1$ and $L^2$ are linking groups;

$R^2$ is $C_xF_y$ or $C_xF_yH_z$ in which x has a value of from 2 to 50, y has a value of from 1 to 2x, and z has a value of 2x-y+1;

M is a hydrophilic homopolymer or copolymer comprising at least three monomeric units each containing at least one atom selected from the group consisting of oxygen and nitrogen;

$R^3$ is (i) hydrogen; or (ii) a monovalent hydrocarbon of 2 to 50 carbon atoms; or (iii) a monovalent fluorinated hydrocarbon of 2 to 50 carbon atoms;

$R^4$ is (i) a bond if $R^3$ is hydrogen; or (ii) $C_xF_y$ or $C_xF_yH_z$; or (iii) a divalent hydrocarbon of 2 to 50 carbon atoms; and each of $L^3$ and $L^4$ taken together with $R^4$, is a bond if $R^3$ is hydrogen or if $R^3$ is other than hydrogen, each of $L^3$ and $L^4$, taken independently is a linking group.

2. The compound of claim 1 in which the value for w is 1.

3. The compound of claim 2 in which M is

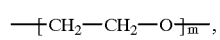

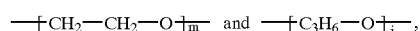

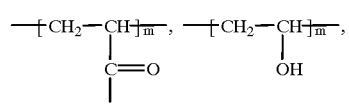

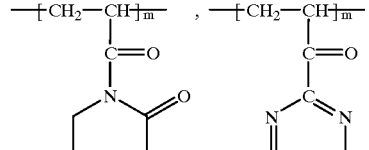

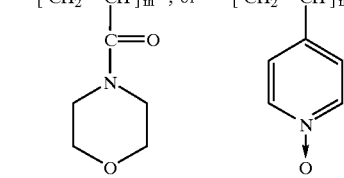

in which each of m and j has a value of from 3 to 5000.

4. The compound of claim 2, in which $R^2$ is $C_xF_y$ and M is $(C_2H_4O)n$, in which n has a value of from 1 to 200, to define the compound having the formula:

$C_qH_{2q+1}$—$L^1$—$C_xF_y$—$L^2$—$(C_2H_4O)_n$—$L^4$—$R^4$—$L^3$—$R^3$.

5. The compound of claim 2, in which each of $L^4$, $R^4$, and $L^3$ is a bond, M is $(C_2H_4O)n$, in which n has a value of from 1 to 200, and $R^3$ is hydrogen to define a compound having the formula:

$C_qH_{2q+1}L^1$—$R^2$—$L^2$—$(C_2H_4O)_n$—H.

6. The compound of claim 2, in which $R^2$ and $R^4$ are $C_xF_yH_z$, and $R^3$ is $C_qH_{2q+1}$ to define a compound having the formula:

$C_qH_{2q+1}$—$L^1$—$R^2$—$L^2$—$(C_2H_4O)_n$—$L^4$—$R^4$—$L^3$—$C_qH_{2q+1}$.

7. The compound of claim 2 in which the linking groups are selected from the group consisting of NH, CONH, NHCOO, NH—CH$_2$—CO—NH, $C_qH_{2q}$—NH, NH—C(NH$_2^+$)CH$_2$CO, NH—C(O)O, NHC(O)(CH$_2$)$_q$C(O)O, N—C(S)—N—(CH$_2$)$_6$—NH, and NC(O)NH(CH$_2$)$_6$NHC(O)—N.

8. The compound of claim 2, in which at least one of $R^2$ and $R^4$ are $C_xF_y$, the value for x is 8, and the value for y is 16.

9. The compound of claim 2 selected from the group consisting of:
(i) C$_{11}$H$_{23}$—CONHC$_2$H$_4$NHCO—C$_8$F$_{16}$—CONHC$_2$H$_4$NHCOO—(C$_2$H$_4$O)$_{34}$—CONHC$_2$H$_4$NHCO—C$_8$F$_{16}$—NHC$_2$H$_4$NHCCO—C$_{11}$H$_{23}$;
(ii) C$_{11}$H$_{23}$—CONHC$_2$H$_4$NHCO—C$_8$F$_{16}$—CONHC$_2$H$_4$NHCOO—(C$_2$H$_4$O)$_{34}$—H;
(iii) C$_{12}$H$_{25}$NHCOC$_8$F$_{16}$CONHC$_2$H$_4$NHCOO—(C$_2$H$_4$O)$_{34}$—CONHC$_2$H$_4$NHCOC$_8$F$_{16}$CONHC$_{12}$H$_{25}$;
(iv) C$_{17}$H$_{35}$—CONHC$_2$H$_4$NHCO—C$_8$F$_{16}$—CONHC$_2$H$_4$NHCOO—(C$_2$H$_4$O)$_{34}$—CONHC$_2$H$_4$NHCO—C$_8$F$_{16}$—NHC$_2$H$_4$NHCO—C$_{17}$H$_{35}$;
(v) C$_{17}$H$_{35}$—CONHC$_2$H$_4$NHCOO—(C$_2$H$_4$O)$_{34}$—CONHC$_2$H$_4$NHCO—C$_{17}$H$_{35}$;
(vi) C$_{11}$H$_{23}$CONHC$_2$H$_4$NHCOO—(C$_2$H$_4$O)$_{34}$—CONHC$_2$H$_4$NHCO—C$_{11}$H$_{23}$; and
(vii) C$_{11}$H$_{23}$—CONHC$_2$H$_4$NHCO—C$_8$F$_{16}$—CONHC$_2$H$_4$NHCOO—(C$_2$H$_4$O)$_{34}$—CONHC$_2$H$_4$NHCO—C$_8$F$_{16}$—NHC$_2$H$_4$NHCO—C$_{11}$H$_{23}$.

10. The compound of claim 2 comprising C$_{11}$H$_{23}$—CONHC$_2$H$_4$NHCO—C$_8$F$_{16}$—CONHC$_2$H$_4$NHCOO—(C$_2$H$_4$O)$_{34}$—H.

11. A pharmaceutical composition comprising a pharmaceutical agent, a pharmaceutically acceptable carrier, and an effective amount of a block co-polymer according to claim 2 for improving the therapeutic index of the agent.

12. A compound having the formula:

$C_qH_{2q+1}$—$L^1$—$C_xF_y$—$L^2$—$(C_2H_4O)_n$—$L^4R^4$—$L^3$—$R^3$ in which:

q has a value of from 2 to 50;

n has a value of from 1 to 200;

x has a value of from 2 to 50;

y has a value of from 1 to 2x;

$L^1$ and $L^2$ are linking groups;

$R^3$ is (i) hydrogen or (ii) a monovalent hydrocarbon of 2 to 50 carbon atoms;

$R^4$ is (i) a bond if $R^3$ is hydrogen or (ii) if $R^3$ is not hydrogen, $C_xF_y$;

$L^3$ and $L^4$ taken together with $R^4$, is a bond if $R^3$ is hydrogen or if $R^3$ is other than hydrogen each of $L^3$ and $L^4$, taken independently is a linking group, in which the linking groups $L^1$, $L^2$, $L^3$ and $L^4$ are selected from the group consisting of NH, CONH, NHCOO, NH—CH$_2$—CO—NH, $C_qH_{2q}$—NH, NH—C(NH$_2^+$)CH$_2$CO, NH—C(O)O, NHC(O)(CH$_2$)$_q$C(O)O, N—C(S)—N—(CH$_2$)$_6$—NH, and NC(O)NH(CH$_2$)$_6$NHC(O)—N.

* * * * *